United States Patent
Smok et al.

(10) Patent No.: US 8,764,663 B2
(45) Date of Patent: Jul. 1, 2014

(54) METHOD AND APPARATUS FOR LOCATING AND DISTINGUISHING BLOOD VESSEL

(71) Applicants: Jeffrey Smok, Westfield, NJ (US); Sheela Blaise, Peoria, IL (US); Sean James Coyle, Tenafly, NJ (US); Lauren Mayer, Glen Ridge, NJ (US); Matt Schurmann, Manchester, NH (US); Daniel Velez, Staten Island, NY (US); Bruce McNair, Holmdel, NJ (US); Vikki Hazelwood, Wayne, NJ (US)

(72) Inventors: Jeffrey Smok, Westfield, NJ (US); Sheela Blaise, Peoria, IL (US); Sean James Coyle, Tenafly, NJ (US); Lauren Mayer, Glen Ridge, NJ (US); Matt Schurmann, Manchester, NH (US); Daniel Velez, Staten Island, NY (US); Bruce McNair, Holmdel, NJ (US); Vikki Hazelwood, Wayne, NJ (US)

( * ) Notice: Subject to any disclaimer, the term of this patent is extended or adjusted under 35 U.S.C. 154(b) by 0 days.

(21) Appl. No.: 13/803,921

(22) Filed: Mar. 14, 2013

(65) Prior Publication Data

US 2013/0197367 A1 Aug. 1, 2013

Related U.S. Application Data

(60) Provisional application No. 61/610,788, filed on Mar. 14, 2012.

(51) Int. Cl.
*A61B 8/00* (2006.01)
*A61B 8/14* (2006.01)

(52) U.S. Cl.
USPC .......................................... 600/454; 600/459

(58) Field of Classification Search
USPC .......... 600/437, 441, 454, 455, 461; 128/916
See application file for complete search history.

(56) References Cited

U.S. PATENT DOCUMENTS

| | | | |
|---|---|---|---|
| 4,515,164 A | 5/1985 | Slavin | |
| 4,582,067 A | 4/1986 | Silverstein et al. | |
| 5,640,960 A * | 6/1997 | Jones et al. | 600/453 |
| 5,910,119 A * | 6/1999 | Lin | 600/455 |
| 6,511,427 B1 * | 1/2003 | Sliwa et al. | 600/438 |
| 6,569,104 B2 | 5/2003 | Ono et al. | |
| 6,755,789 B2 * | 6/2004 | Stringer et al. | 600/461 |
| 2005/0150309 A1 | 7/2005 | Beard | |
| 2012/0059264 A1 | 3/2012 | Hope Simpson et al. | |

FOREIGN PATENT DOCUMENTS

| | | |
|---|---|---|
| EP | 0102733 | 10/1986 |
| EP | 1495712 | 12/2005 |
| WO | 2005006952 | 1/2005 |

OTHER PUBLICATIONS

University of Connecticut, Electrical and Computer Engineering Department, "Doppler Ultrasound Flow Detector, Project Proposal: Senior Design Team 6, ECE 290", 10 pages, Spring 2006.
http://www.1cascade.com/category.aspx?categoryID=10026, [retrieved: Feb. 16, 2013], 1 page.
http://www.edanusa.com/Product/SonoTrax-II-Fetal-Doppler-Baby-Heart-Monitor.html, [retrieved: Feb. 16, 2013], 2 pages.
http://www.cardinal.com/us/en/distributedproducts/ASP/EN50.asp?cat=med_surg, [retrieved: Feb. 16, 2013], 1 page.

(Continued)

*Primary Examiner* — Michael Rozanski
(74) *Attorney, Agent, or Firm* — Lowenstein Sandler LLP

(57) ABSTRACT

A apparatus and a method are disclosed for transmitting a signal directed to a blood vessel via a Doppler ultrasound waveform apparatus, receiving, by the Doppler ultrasound waveform apparatus, a reflected signal from the blood vessel; and determining, by a processing device, whether the blood vessel is an artery or a vein based on a blood flow velocity in the blood vessel.

10 Claims, 8 Drawing Sheets

(56) References Cited

OTHER PUBLICATIONS http://www.summitdoppler.com/site/epage/106923_969.htm, [retrieved: Feb. 16, 2013], 1 page.

http://www.huntleigh-diagnostics.conn/diagnostics/us/Product.asp?PageNumber=2621&Product_Id=419&ProductCategory_Id=215, [retrieved: Feb. 16, 2013], 1 page.

* cited by examiner

METHOD AND APPARATUS FOR LOCATING AND DISTINGUISHING BLOOD VESSEL

RELATED APPLICATIONS

The present application claims the benefit of U.S. Provisional Application Ser. No. 61/610,788, titled "Visual Expedient Inexpensive Nimble UltraSound (VEINUS)," filed on Mar. 14, 2012, the entire contents of which are herein incorporated by reference.

TECHNICAL FIELD

The present disclosure relates to the field of medical monitoring and diagnostic procedures and devices. Specifically, the present disclosure relates to a Doppler ultrasound method and apparatus for locating and distinguishing blood vessels.

BACKGROUND

Medical professionals have long sought for a way to utilize ultrasound technology to help place intravenous catheters and needles in a patient more effectively. There often is a medical need to locate a blood vessel and to distinguish whether the blood vessel is a vein or an artery. For example, a vein is typically used for applying an intravenous (IV) medication, while an artery may be used for inserting a catheter to accomplish certain medical procedures. In addition, IV or catheter placement, and other medical therapies requiring blood collection, often present medical professionals with difficulties in pinpointing the exact location of a blood vessel. This can be due to many reasons including the patient's age, weight or complexion, and also the experience of the medical professionals who may be administering IV or catheter. The difficulties in locating and distinguishing a blood vessel are due in part to the fact that the current standard for locating blood vessels relies mainly on the touch and sight of the medical professional.

There are many factors that affect the visibility of the blood vessels. In turn, this can affect how many times a patient will have to be stuck with a needle. Obesity is one reason why it may be difficult to locate veins and arteries. Dehydration can also make it difficult for medical professional to locate a blood vessel to administer a medication to a patient via intravenous therapy. Other medical conditions such as venous thrombosis (a clogged vein), necrosis (death of tissue cells) and an embolus (air bubble in a blood vessel) can prohibit proper injection of medication using IV therapy or make it difficult to draw blood.

When the medical professional believes that an appropriate blood vessel has been located, he or she places a needle in the location of the blood vessel to perform the medical procedure. In many cases the medical professional may have been incorrect or that the needle may not have placed in a suitable blood vessel, thereby subjecting the patient to further needle sticks. For instance, of the over 1 Billion IV placements performed in the US each year, at least 300 Million placements will miss the blood vessel on the first attempt. And every failed needle stick subjects the patient to additional pain and injury.

There are numerous techniques that medical professionals typically use to help find blood vessels that are difficult to locate. These techniques aim to increase the visibility of blood vessels under the patient's skin. Options for assisting with intravenous (IV) and catheter placement have become available in recent years include infrared technology and modified sonograph machines. The current infrared devices require the medical professional to have the device held by another person while they place IV needle or a catheter into a blood vessel. Traditional sonograph machines can be very large, bulky, and stationary. Modified sonograph machines that only make use of a single transducer cannot distinguish whether the location is directly over a blood vessel or just off of an edge of the blood vessel, which can lead to an improper placement of an IV needle or catheter. Other sonograph machines may use techniques such as pulsed-wave Doppler (PW), which typically requires high-voltage (e.g., a driving signal at approximately 200 volts) and precision timing for the transducers, or continuous wave Doppler (CW), which requires a second set of transducers, which increases costs. Because of these reasons, among others, ultrasound and infrared technology has not widely been used for detecting and locating blood vessels.

BRIEF DESCRIPTION OF THE DRAWINGS

Implementations of the present disclosure will be understood more fully from the detailed description given below and from the accompanying drawings of various implementations of the disclosure, which should not be taken to limit the disclosure to the specific aspects or implementations, but are for explanation and understanding.

DETAILED DESCRIPTION

Methods and systems for locating and distinguishing blood vessels are described. In certain embodiments, the present invention is directed to methods and systems for utilizing a sonograph device (e.g., a handheld and/or wireless device) that can use any Doppler technique such as tone-burst excitation, a form of differential Doppler ultrasound, which utilizes dual ultrasonic transducers that can detect and distinguish veins from arteries by assessing the velocities of a blood flow in a blood vessel. The methods can locate and distinguish blood vessels without needing to stick a patient with a needle to determine if a medical professional has indeed found the blood vessel. A transducer can transmit pulse ultrasound waves into a patient's blood vessel at a standard frequency, and can receive the reflected ultrasound waves at a shifted frequency due to the speed of the blood in the blood vessel. This frequency shift can be processed to locate a blood vessel, determine whether the blood vessel is an artery or a vein, and can provide a level of confidence as to whether the blood vessel is an artery or a vein.

In the following description, numerous details are set forth. It will be apparent to one of ordinary skill in the art having the benefit of this disclosure that examples of the present teachings may be practiced in the absence of these specific details. In some instances, well-known structures and devices are shown in block diagram form instead of in detail in order to avoid obscuring the examples of the present teachings.

Figure 1:
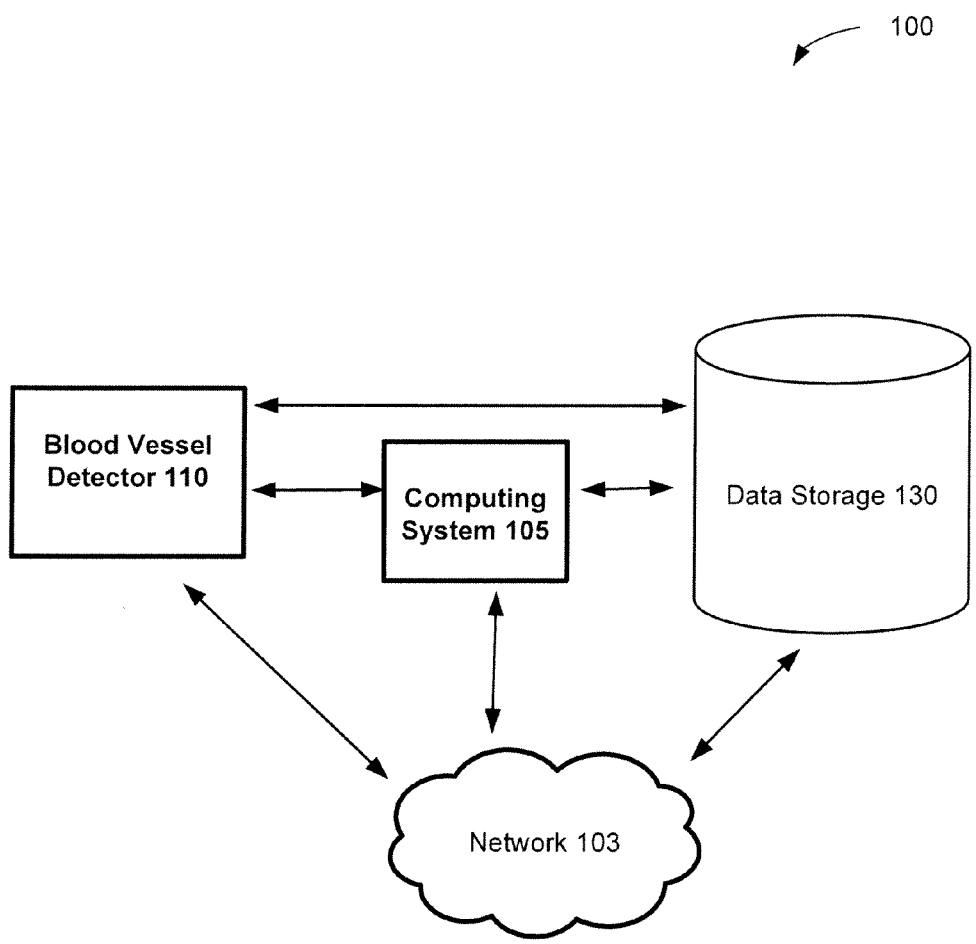
FIG. 1 is a block diagram of a network architecture in which examples of methods and systems for locating and distinguishing blood vessels may operate in accordance with the present disclosure.

FIG. 1 is a block diagram of a network architecture 100 in which examples of methods and systems for locating and distinguishing blood vessels may operate in accordance with the present disclosure. In the depicted example, the network architecture 100 includes a blood vessel detector 110, a computing system 105, a network 103, and a data storage 130. The blood vessel detector 110 may interact with the computing system 105 and with the data storage 130 via the network 103.

The blood vessel detector 110 may be a device that can be placed on or near a specific area of a body (e.g., an arm, a leg, the torso, or the like) to provide feedback that can indicate the location of a blood vessel and also can indicate whether the blood vessel is an artery or a vein with a level of confidence. The blood vessel detector 110 can be communicatively coupled to the network 103, which may include the Internet and network connections to the Internet. Alternatively, the blood vessel detector 110 may be communicatively coupled to a common local area network (LAN), personal area network (PAN), campus area network (CAN), metropolitan area network (MAN), Wide area network (WAN), wireless local area network, cellular network, virtual local area network, or the like. The blood vessel detector can also be communicatively coupled to a computing system 105 which may include a consumer workstation, a server, a computer, a portable electronic device, an entertainment system configured to communicate over a network, such as a set-top box, a digital receiver, a digital television, a mobile phone, or other electronic devices. For example, portable electronic devices may include, but are not limited to, cellular phones, portable gaming systems, portable computing devices, or the like. The computing system 105 may have access to the Internet via a firewall, a router, or other packet switching devices. The computing system 105 may be a network appliance, a gateway, a personal computer, a desktop computer, a workstation, etc. The data storage 130 may be a computer readable medium that is responsible for storing data from the blood vessel detector 110.

The blood vessel detector 110 can include an outer casing that may be constructed from medical grade material that can be sterilized and used in environments that require sterile medical equipment, such as in a surgical setting. For example, a medical grade high pressure polyethylene material, or similar materials that are resistant to corrosive chemicals that are typically used in medical environments, could be used to construct the outer casing of the blood vessel detector 110. As such, the blood vessel detector 110 may be sterilized via UV sterilization techniques or may be placed in an autoclave for sterilization, or the like.

Figure 2:
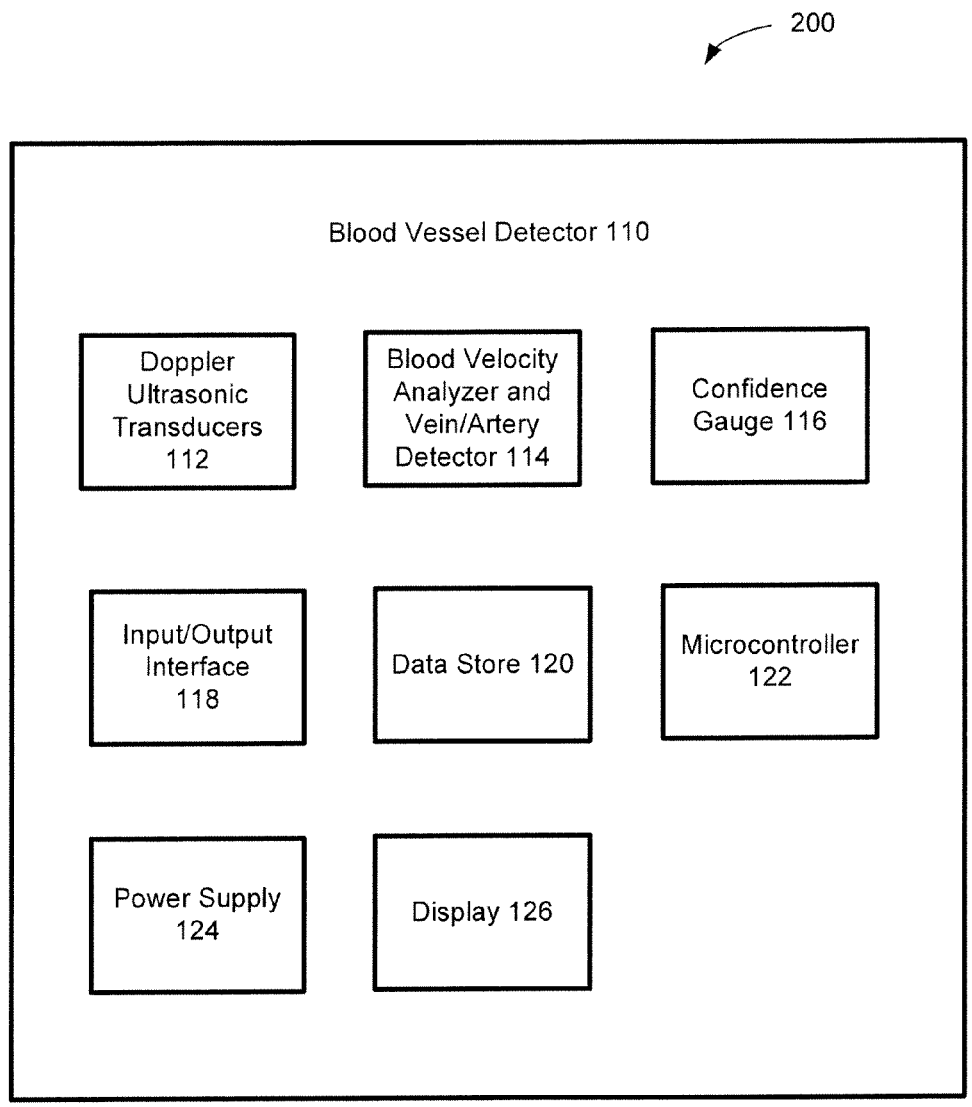
FIG. 2 is a block diagram of an example for providing methods and systems for locating and distinguishing blood vessels in accordance with some implementations of the present disclosure.

FIG. 2 is a block diagram of an example for providing methods and systems 200 for locating and distinguishing blood vessels in accordance with some implementations of the present disclosure. In the example, the block diagram illustrates a blood vessel detector 110 that includes dual Doppler ultrasonic transducers 112, a blood velocity analyzer and vein/artery detector 114, a confidence gauge 116, an input/output interface 118, a data store 120, a microcontroller 122, a power supply 124, and a display 126.

The blood vessel detector 110 may use a differential Doppler ultrasound configuration to locate a blood vessel and determine whether the located blood vessel is an artery or a vein. The differential Doppler ultrasound configuration may use dual Doppler ultrasound transducers 112 within the blood vessel detector 110. Each of the dual Doppler ultrasound transducers 112 can transmit short ultrasonic tones into a body tissue towards a blood vessel. The dual Doppler ultrasound transducers 112 can then receive the reflected tones from the moving blood, upon which a comparative measurement can be made based on the Doppler shift and on statistics calculated from the reflected signal. The use of dual Doppler ultrasound transducers 112 can provide the blood vessel detector 110 with a greater accuracy in the location of the blood vessel as the second transducer can enable a comparative measurement decision is made based on statistics calculated from each reflected signal. The second transducer can thus determine and confirm whether the first transducer is receiving a blood flow or an artifact or noise.

In an example, the Doppler ultrasound transducers 112 may be piezoelectric non-destructive testing (NDT) transducers transducers, such that electrical signals can be used to cause the Doppler ultrasound transducers 112 generate and transmit ultrasonic tones, and the sonic reflections can received by the Doppler ultrasound transducers 112 and can be converted into electrical signals for further conditioning, sampling, and processing.

The blood vessel detector 110 may also include a crystal oscillator and a transmit amplifier to drive the transducers near resonance to reduce power requirements. The Doppler ultrasound transducers 112 may have a resonant frequency that can range from 1.0 MHz to 10.0 MHz. The selection of the resonant frequency of the Doppler ultrasound transducers 112 is discussed in further detail below in the discussion with respect to FIG. 4.

The blood velocity analyzer 114 of FIG. 2 may determine the velocity of a blood flow based on a Doppler shift, which can be determined based on information received from the Doppler ultrasound transducers 112. The Doppler Shift observed, $\Delta f$, is proportional to the ratio of the velocity of the blood, V, to the speed of sound in the body, C, and the contact angle of the ultrasonic tone & moving blood, $\alpha$, when multiplied by twice the resonant frequency, $f_o$. An equation for calculating the observed Doppler shift is as follows:

$$\Delta f = 2f_o(V/C)\cos(\alpha).$$

This yields the following equation:

$$V_{blood} = (C_{tissue}/2 \cos(\alpha))(f_o - f_{doppler}),$$

where $V_{blood}$ is the velocity of the blood flow in the blood vessel, $C_{tissue}$ is a speed of sound in soft tissue, a is an angle of incidence of the ultrasound waveform apparatus, $f_o$ is the resonant frequency of the ultrasound waveform apparatus, and $f_{doppler}$ is the frequency of the Doppler shifted echo.

A preferred angle, $\alpha$, for ultrasound transducers can be between 30° and 60° from the blood vessel. If the ultrasound transducers are held perpendicular to the blood vessel, (e.g., at 90°), the equation will yield no Doppler shift, as the cos (90°)=0. A preferred angle of incidence can be 45°. At this angle, the distance between the blood vessel and the transducers would be the same vertically as the pulse and transducers would be horizontally.

The blood velocity analyzer 114 of FIG. 2 can include programming logic that can determine whether a blood vessel is a vein or an artery based on the velocity of the blood flow, as the velocity of the blood flow is higher in an artery than it is in a vein at a given location in a normal body. For example, in a normal adult human, the blood velocity in the Radial Artery of the left arm has a range of approximately 60 to 100 cm/sec., while the blood velocity in the Cephalic Vein in the left arm has a range of about 10 to 20 cm/sec. The blood velocity analyzer 114 can determine whether the blood vessel is an artery or a vein based on the absolute value of The Doppler Shift observed, Δf, from which the velocity of the blood flow in the blood vessel $V_{blood}$ can be determined. When the velocity of the blood flow in the blood vessel $V_{blood}$ falls in an expected range of an artery, the blood velocity analyzer 114 can determine that the blood vessel is an artery. Likewise, when the velocity of the blood flow in the blood vessel $V_{blood}$ falls in an expected range of a vein, the blood velocity analyzer 114 can determine that the blood vessel is a vein.

The confidence gauge 116 of FIG. 2 can include programming logic to determine a level of confidence in the determination of whether the blood vessel is an artery or a vein. A range of velocities may be available to identify whether the vessel is an artery or a vein. For example, as stated above, the blood velocity of the Cephalic Vein may range between 10 to 20 cm/sec in normal adults. If the measured velocity is, for instance, 15 cm/sec, the confidence gauge 116 can show a high confidence percentage that it has found a vein because the measured velocity of the blood flow falls directly in the center of the range. However if the measured velocity is, for example, 10 cm/sec, the confidence gauge 116 can show a lower confidence percentage since the measured blood flow velocity is on the outskirts of the range.

The blood vessel detector 110 may include an input/output interface 118 that may be a transmitter and/or receiver that can be capable of communicating with other devices via the network 103. In an example, the blood vessel detector 110 can communicates with the network 103 via a wireless connection using wireless network protocols such as, but not limited to, Bluetooth®.

The blood vessel detector 110 may include a data store 120, a microcontroller 122, and a power supply 124. The data store 120 may be a computer readable medium for storing data and programming logic for locating and distinguishing blood vessels. The microcontroller 122 may process and facilitate the programming logic for locating and distinguishing blood vessels. As used herein, the term "microcontroller" can be a "processor" or a "processing device" which is intended to include, but is not limited to, a programmable electronic machine that performs executes software to perform several operations such as assemble, store, correlate, or otherwise processes information. The power supply 124 may be a device such as a battery that can deliver electrical power as an energy source to operate the blood vessel detector 110. In an example, the power supply 124 may be a rechargeable battery.

The blood vessel detector 110 may include a display 126. In an example, the display 126 may be an illuminating indicator that may include light-emitting diodes (LED), a liquid crystal display (LCD), or the like. The display 126 may be configured to indicate whether a blood vessel is an artery or a vein, and may also indicate a confidence level as to whether the blood vessel is an artery or a vein.

Figure 3:
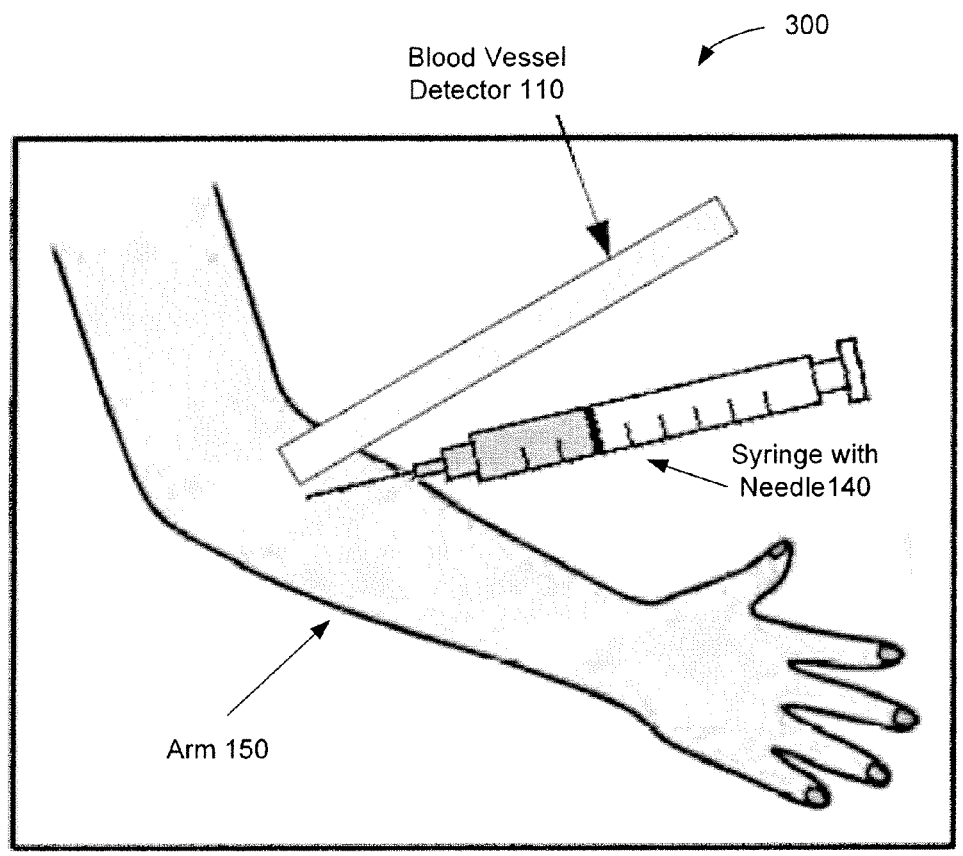
FIG. 3 is a diagram of an example of methods and systems for locating and distinguishing blood vessels in accordance with some implementations of the present disclosure.

FIG. 3 is a diagram of an example of methods and systems 300 for locating and distinguishing blood vessels in accordance with some implementations of the present disclosure. The example includes a blood vessel detector 110, a syringe with needle 140, and an area of a body for locating and distinguishing blood vessels, in this example, an arm 150.

In the example 300, the blood vessel detector 110 may be used by a medical professional to locate and distinguish the blood vessels that are in the arm 150. It is understood that the area of a body for locating and distinguishing blood vessels may be other parts of a body, such as a leg, calf, torso, and the like. It is also understood that the area of the body may be human or non-human.

In the example illustrated in FIG. 3, the medical professional may position the blood vessel detector 110 on the arm 150. The blood vessel detector 110 can measure the velocity of the blood flow in the blood vessels in the arm 150. When the blood vessel detector 110 is positioned directly over a blood vessel, the blood vessel detector 110 can indicate whether the blood vessel is an artery or a vein. The blood vessel detector 110 can also indicate a level of confidence as to whether the blood vessel is an artery or a vein. The medical professional can use the location of the blood vessel to insert a syringe with needle 140 or to insert a catheter (not shown).

Figure 4:
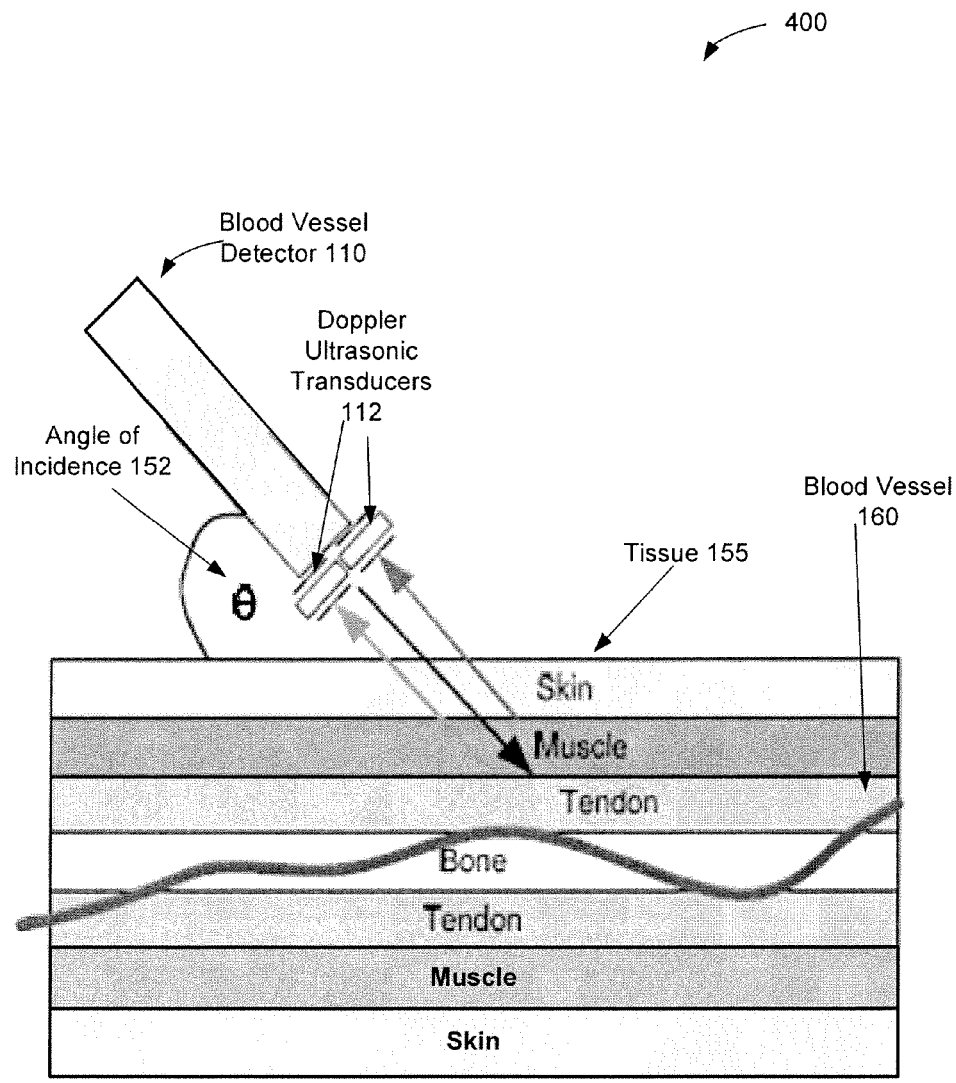
FIG. 4 is a diagram of an example of methods and systems for locating and distinguishing blood vessels in accordance with some implementations of the present disclosure.

FIG. 4 is a diagram of an example of methods and systems 400 for locating and distinguishing blood vessels in accordance with some implementations of the present disclosure. The example includes the blood vessel detector 110 having dual Doppler ultrasonic transducers 112, and illustrates a cross-section view of tissue 155 that includes layers representing skin, muscle, tendon, bone, tendon, muscle, and skin. The tissue also includes a blood vessel 160. The angle of incidence 152 is the angle of the dual Doppler ultrasonic transducers 112 relative to a horizontal plane of the tissue 155.

As discussed above, the Doppler ultrasound transducers 112 may have a resonant frequency that can range from 1.0 MHz to 10.0 MHz. The selection of the resonant frequency of the Doppler ultrasound transducers 112 can affect the functionality of their ability to detect blood vessels at different depths within the tissue 155 because a change in resonant frequency of the Doppler ultrasound transducers 112 is inversely proportional to the depth of penetration of the transmission of the ultrasonic waves. For example, the greater the resonant frequency of the Doppler ultrasound transducers 112, the shallower the penetration of the ultrasonic waves. In an example, the resonant frequency of the Doppler ultrasound transducers 112 may be approximately 2.25 MHz, in which such a frequency may enable the blood vessel detector 110 to detect blood vessels as deep as 7 cm from the skin surface.

Figure 5:
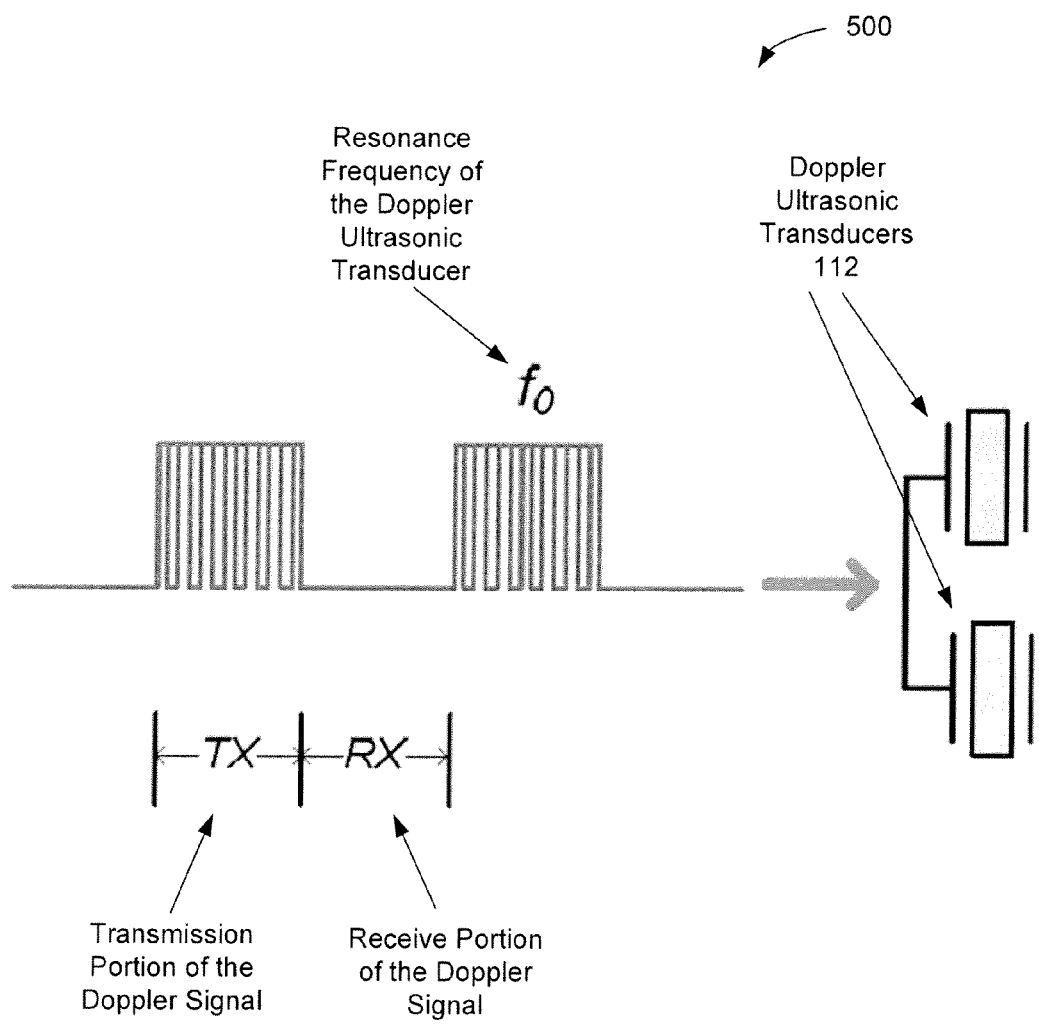
FIG. 5 is an example for providing methods and systems for locating and distinguishing blood vessels in accordance with some implementations of the present disclosure.

FIG. 5 is an example for providing methods and systems 500 for locating and distinguishing blood vessels in accordance with some implementations of the present disclosure. The example method 500 illustrates a representation of tone-burst excitation.

The present disclosure may can use any Doppler technique such as pulsed-wave Doppler (PW) and continuous wave Doppler (CW). In the example method 500, the Doppler ultrasound transducers 112 may be driven via tone-burst excitation. Tone-burst excitation is essentially a cross between the more familiar techniques of PW and CW. Tone-burst excitation uses a signal near the resonant frequency of the transducers as a driving signal, causing the transducers to vibrate and emit ultrasonic energy. Tone-burst excitation may be selected over PW or CW for a number of reasons. Unlike CW, the Doppler ultrasound transducers 112 in tone-burst excitation are not driven persistently because the driving signal is removed periodically to allow the Doppler ultrasound transducers 112 to receive the Doppler shifted echoes created as the tone travels through the body. Unlike PW, which typically requires high-voltage (e.g., a driving signal at approximately 200 volts), the driving signals for tone-burst excitation are substantially lower.

In an example, the tone-burst excitation method can use a low-amplitude oscillatory input signal, such as from a crystal oscillator, at the resonance frequency $f_o$ of the transducer to efficiently couple energy into the transducer, which can cause the transducer to vibrate at its resonance frequency. The use of tone-burst excitation can enable the blood vessel detector 110 to handle both dual transmission (i.e., the "TX" portion of the signal) and reception (i.e., the "RX" portion of the signal) while requiring only two ultrasonic transducers. During the silent portion of the driving signal, the Doppler ultrasound transducers 112 can be switched to a receiver-chain which allows the blood vessel detector 110 to receive the Doppler-shifted echoes.

Figure 6:
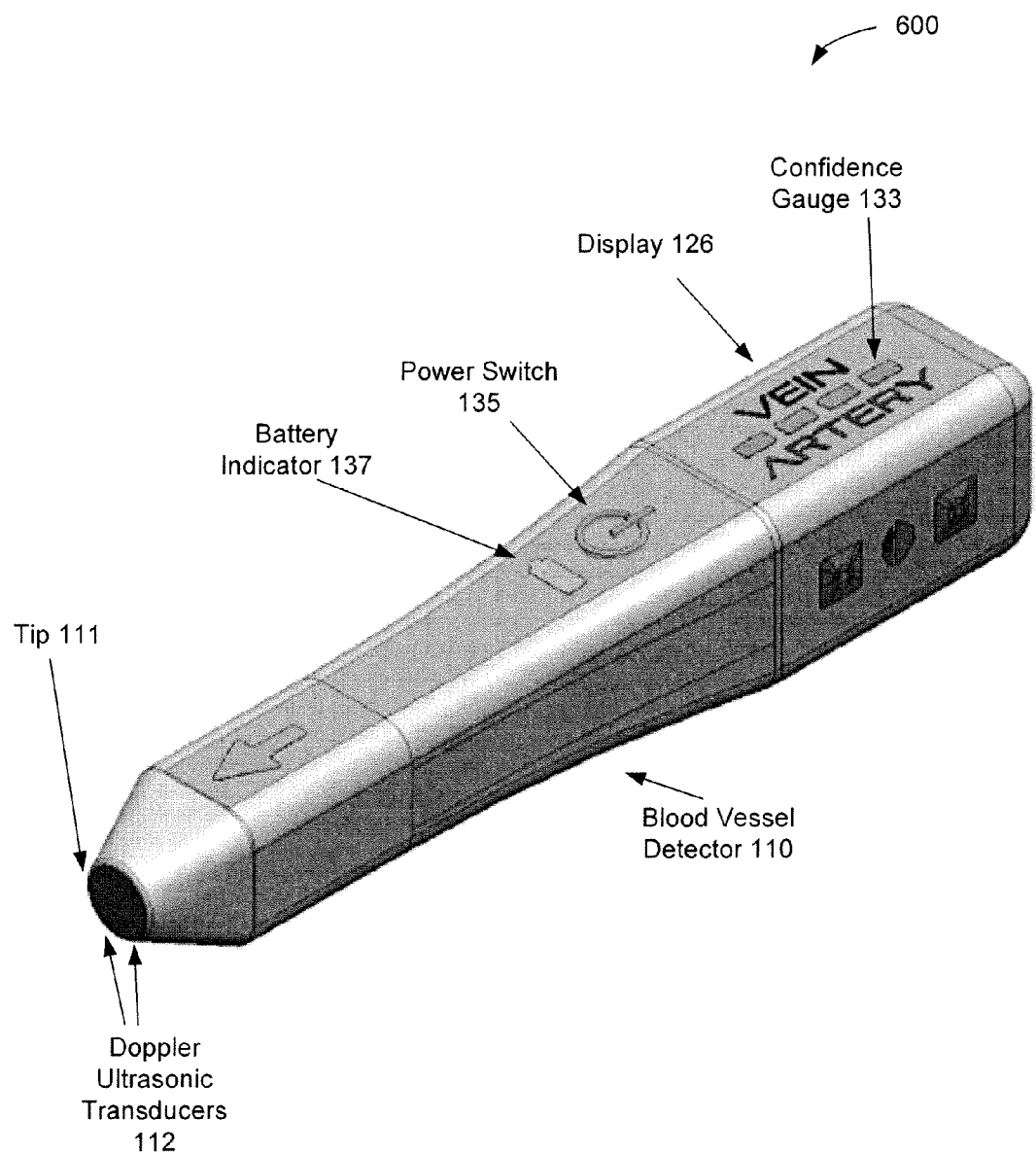
FIG. 6 is a diagram of an example of methods and systems for locating and distinguishing blood vessels in accordance with some implementations of the present disclosure.

FIG. 6 is a diagram of an example of methods and systems 600 for locating and distinguishing blood vessels in accordance with some implementations of the present disclosure. The example of FIG. 6 illustrates a blood vessel detector 110 including a tip 111, dual Doppler ultrasound transducers 112, a display 126, a confidence gauge 133, a power switch 135 to turn on and off the power to the blood vessel 110, and a battery indicator 137 that may indicate the charge of the battery.

The dual Doppler ultrasound transducers 112 may be mounted into a tip 111 which may protrude from the housing of the blood vessel detector 110. In an example, the tip 111 may be conically shaped. The display 126 may be an illuminating indicator that may include light-emitting diodes (LED), a liquid crystal display (LCD), or the like. The display 126 may be configured to indicate whether a blood vessel is an artery or a vein. For example, when the blood vessel detector 110 determines that the blood vessel is an artery, the display 126 may illuminate the word "artery." Similarly, when the blood vessel detector 110 determines that the blood vessel is a vein, the display 126 may illuminate the word "vein."

The display 126 may also be configured to include a confidence gauge 133 to indicate a confidence level as to whether a blood vessel is an artery or a vein. For example, when the blood vessel detector 110 determines that the blood vessel is an artery and the display 126 illuminates the word "artery," the display 126 may also illuminate a set of lights on the confidence gauge 133 to indicate a level of confidence that the blood vessel is an artery. The number of lights on the confidence gauge 133 that may be illuminated can be representative of the level of confidence, e.g., all the lights may be illuminated at the highest level of confidence, while only one light may be illuminated when the level of confidence is low.

Figure 7:
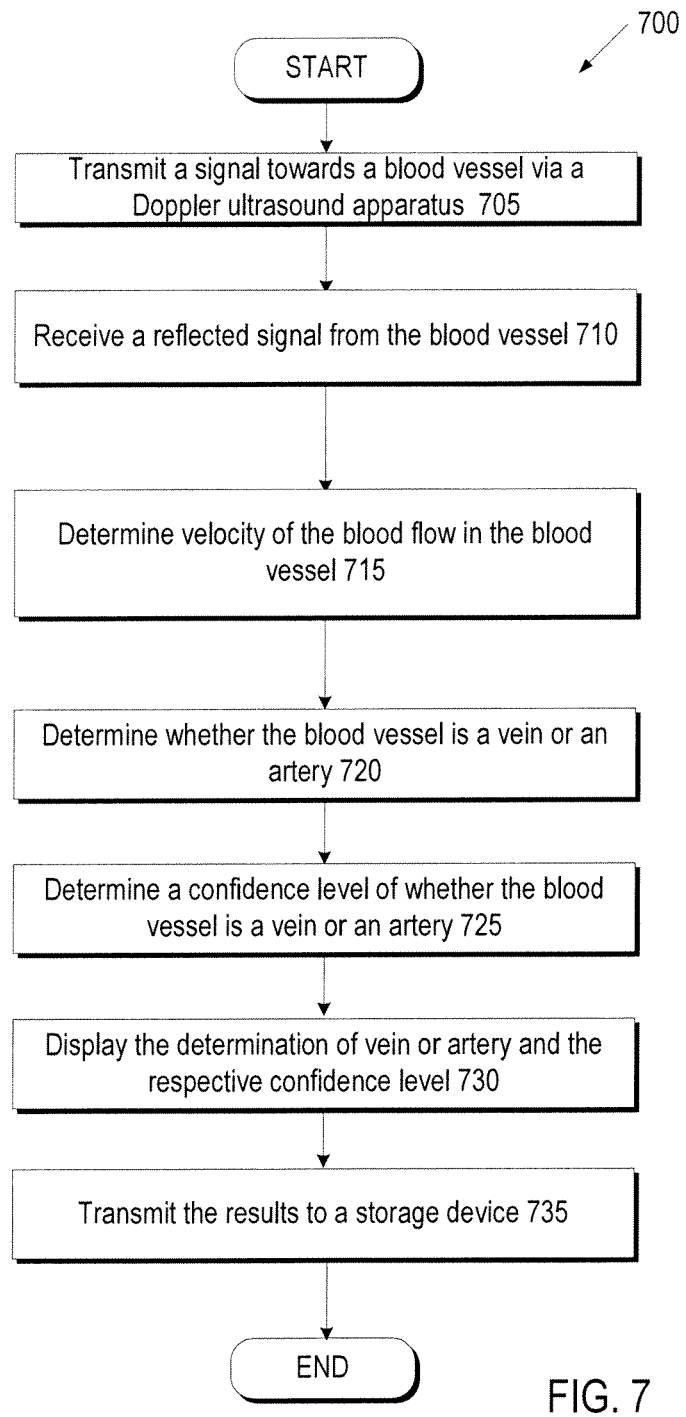
FIG. 7 is a flow diagram illustrating an example of a method for providing methods and systems for locating and distinguishing blood vessels in accordance with some implementations of the present disclosure.

FIG. 7 is a flow diagram illustrating an example of a method 700 for providing methods and systems for locating and distinguishing blood vessels in accordance with some implements of the present disclosure. The method 700 can be performed by processing logic that may comprise hardware (circuitry, dedicated logic, a processing device, etc.), software (such may be executed on a general-purpose computing system, a processing device, or a dedicated machine), or a combination of both.

At block 705, the processing logic may begin the workflow by enabling the blood vessel detector 110 to transmit a signal towards a blood vessel. At block 710, the blood vessel detector 110 may receive a reflected signal from the blood vessel. At block 715, the processing logic may determine velocity of the blood flow in the blood vessel based on the frequency of the Doppler shift. At block 720, the processing logic may determine whether the blood vessel is a vein or an artery. At block 725, the processing logic may determine a confidence level of whether the blood vessel is a vein or an artery. At block 730, the blood vessel detector 110 may determine display the determination of vein or artery and the respective confidence level. At block 735 the blood vessel detector 110 may transmit the results to a storage device 130, and the method 900 ends.

Figure 8:
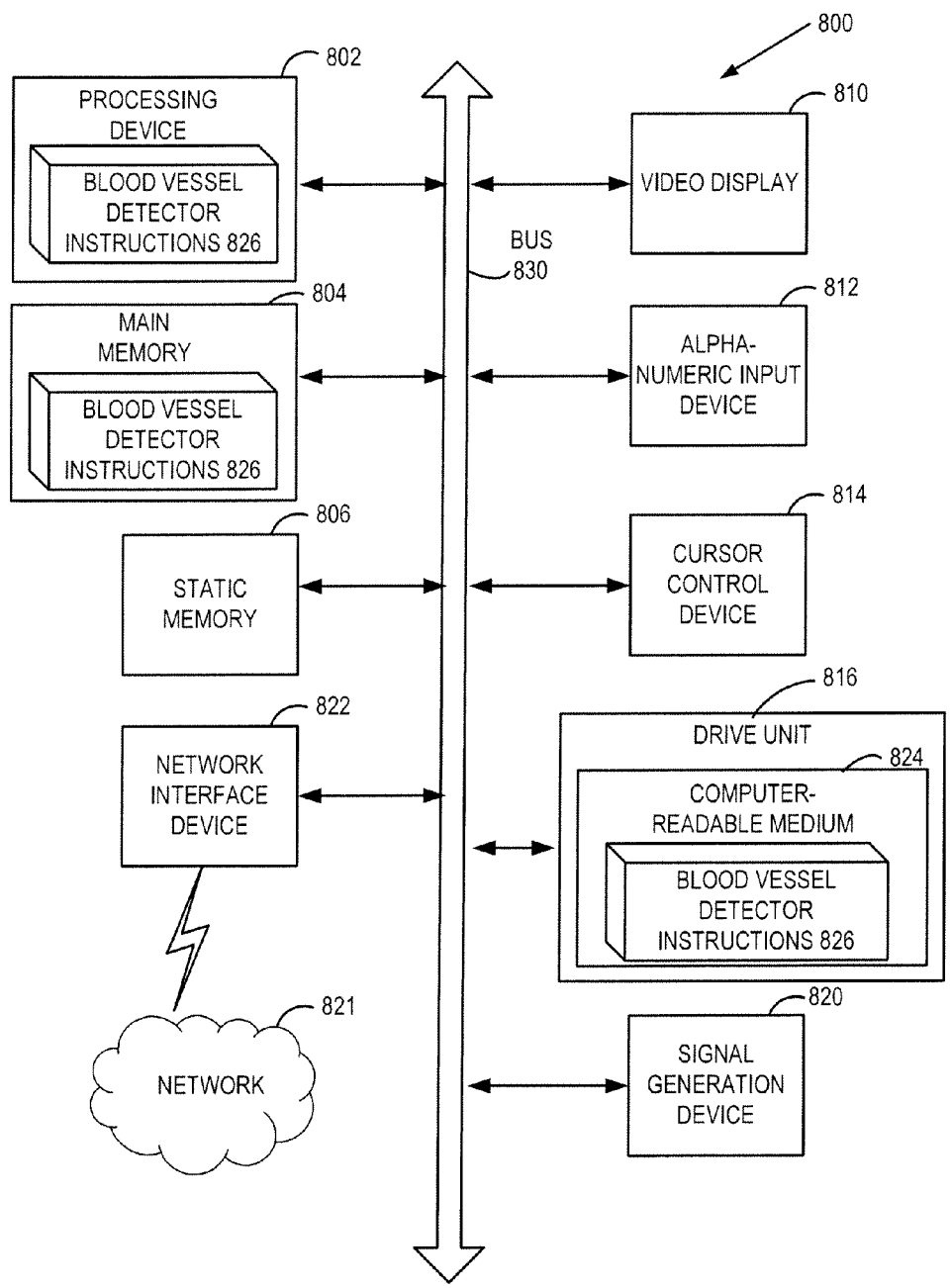
FIG. 8 illustrates a diagrammatic representation of a machine in the form of a computer system, in accordance with one example.

FIG. 8 illustrates a diagrammatic representation of a machine in the form of a computer system, in accordance with one example. The computing system may include a set of instructions 826, for causing the machine to perform any one or more of the methodologies discussed herein. In alternative examples, the machine may be connected (e.g., networked) to other machines in a Local Area Network (LAN), an intranet, an extranet, or the Internet. The machine may operate in the capacity of a server or a client machine in a client-server network environment, or as a peer machine in a peer-to-peer (or distributed) network environment. The machine may be a personal computer (PC), a tablet PC, a set-top box (STB), a Personal Digital Assistant (PDA), a cellular telephone, a web appliance, a server, a network router, switch or bridge, or any machine capable of executing a set of instructions (sequential or otherwise) that specify actions to be taken by that machine. Further, while a single machine is illustrated, the term "machine" shall also be taken to include any collection of machines (e.g., computers) that individually or jointly execute a set (or multiple sets) of instructions to perform any one or more of the methodologies discussed herein.

The computer system 800 includes a processing device 802, a main memory 804 (e.g., read-only memory (ROM), flash memory, dynamic random access memory (DRAM) such as synchronous DRAM (SDRAM), etc.), a static memory 806 (e.g., flash memory, static random access memory (SRAM), etc.), and a secondary memory 816 (e.g., a data storage device), which communicate with each other via a bus 830.

The processing device 802 represents one or more general-purpose processing devices such as a microprocessor, central processing unit, or the like. More particularly, the processing device 802 may be a complex instruction set computing (CISC) microprocessor, reduced instruction set computing (RISC) microprocessor, very long instruction word (VLIW) microprocessor, processor implementing other instruction sets, or processors implementing a combination of instruction sets. The processing device 802 may also be one or more special-purpose processing devices such as an application specific integrated circuit (ASIC), a field programmable gate array (FPGA), a digital signal processor (DSP), network processor, or the like. The processing device 802 is configured to execute the operations for the blood vessel detector 110 for performing steps discussed herein.

The computer system 800 may further include a network interface device 822. The network interface device may be in communication with a network 821. The computer system 800 also may include a video display unit 810 (e.g., a liquid crystal display (LCD), a touch screen, or a cathode ray tube (CRT)), an alphanumeric input device 812 (e.g., a keyboard), a cursor control device 814 (e.g., a mouse), and a signal generation device 820 (e.g., a speaker).

The secondary memory 816 may include a computer-readable storage medium (or more specifically a non-transitory computer-readable storage medium) 824 on which is stored one or more sets of instructions 826 (e.g., instructions executed by the blood vessel detector 110) for the computer system 800 representing any one or more of the methodologies or functions described herein. The instructions 826 for the computer system 800 may also reside, completely or at least partially, within the main memory 804 and/or within the processing device 802 during execution thereof by the computer system 800, the main memory 804 and the processing device 802 also constituting computer-readable storage media. The instructions 826 for the computer system 800 may further be transmitted or received over a network via the network interface device 822.

While the computer-readable storage medium 824 is shown in an example to be a single medium, the term "computer-readable storage medium" should be taken to include a single medium or multiple media (e.g., a centralized or distributed database, and/or associated caches and servers) that store the one or more sets of instructions 826. The term "computer-readable storage medium" shall also be taken to include any medium that is capable of storing or encoding a set of instructions for execution by the machine that cause the machine to perform any one or more of the methodologies of the disclosure. The term "computer-readable storage medium" shall accordingly be taken to include, but not be limited to, solid-state memories, and optical and magnetic media.

Some portions of the detailed descriptions above are presented in terms of symbolic representations of operations on data bits within a computer memory. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, as apparent from the following discussion, it is appreciated that throughout the description, discussions utilizing terms such as "configuring," "associating," "executing," "adjusting," "sending," "receiving," "determining," "transmitting," "identifying," "specifying," "granting," "accessing," "assigning," "detecting," and "requesting," or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The disclosure also relates to an apparatus for performing the operations herein. This apparatus may be specially constructed for the required purposes, or it may be a general purpose computer system selectively programmed by a computer program stored in the computer system. Such a computer program may be stored in a computer readable storage medium, such as, but not limited to, any type of disk including optical disks, CD-ROMs, and magnetic-optical disks, read-only memories (ROMs), random access memories (RAMs), EPROMs, EEPROMs, magnetic disk storage media, optical storage media, flash memory devices, other type of machine-accessible storage media, or any type of media suitable for storing electronic instructions, each coupled to a computer system bus.

The descriptions and displays presented herein are not inherently related to any particular computer or other apparatus. Various general purpose systems may be used with programs in accordance with the teachings herein, or it may prove convenient to construct a more specialized apparatus to perform the required method steps. The required structure for a variety of these systems will appear as set forth in the description below. In addition, the disclosure is not described with reference to any particular programming language. It will be appreciated that a variety of programming languages may be used to implement the teachings of the disclosure as described herein.

It is to be understood that the above description is intended to be illustrative, and not restrictive. Many other examples will be apparent to those of skill in the art upon reading and understanding the above description. Although the disclosure has been described with reference to specific examples, it will be recognized that the disclosure is not limited to the examples described, but can be practiced with modification and alteration within the spirit and scope of the appended claims. Accordingly, the specification and drawings are to be regarded in an illustrative sense rather than a restrictive sense. The scope of the disclosure should, therefore, be determined with reference to the appended claims, along with the full scope of equivalents to which such claims are entitled.

What is claimed is:

1. A method comprising:
    transmitting a signal directed to a blood vessel via a self-contained, battery operated, wireless, and autoclavable Doppler ultrasound waveform apparatus comprising a confidence gauge to indicate a confidence level of an artery or a vein, wherein the confidence gauge comprises a plurality of lights and wherein a number of illuminated lights of the plurality of lights indicates the confidence level;
    receiving, by the Doppler ultrasound waveform apparatus, a reflected signal from the blood vessel;
    determining, by a processing device, whether the blood vessel is an artery or a vein based on a blood flow velocity in the blood vessel;
    determining, by the processing device, a confidence level as to whether the blood vessel is an artery or a vein; and
    displaying the confidence level on the confidence gauge.

2. The method of claim 1, further comprising determining a phase of a Doppler shift and transmitting the results to a file.

3. The method of claim 1, wherein the Doppler ultrasound waveform apparatus is a tone burst excitation differential Doppler apparatus, further comprising:
    determining a location of the blood vessel; and
    displaying an indication of the location of the blood vessel.

4. The method of claim 1, wherein the blood vessel is located in a human arm, further comprising:
    determining that the blood vessel is an artery when the blood flow velocity is between 60 cm/sec and 100 cm/sec; and
    determining that the blood vessel is a vein when the blood flow velocity is between 10 cm/sec and 20 cm/sec.

5. The method of claim 4, further comprising:
    determining a high confidence level that the blood vessel is an artery when the blood flow velocity is between 75 cm/sec and 85 cm/sec; and
    determining a high confidence level that the blood vessel is a vein when the blood flow velocity is between 14 cm/sec and 16 cm/sec.

6. The method of claim 1, further comprising determining the blood flow velocity based on an equation, wherein the equation is:

$$V_{blood} = (C_{tissue}/2 \cos(\alpha))(f_o - f_{doppler})$$

wherein:
    $V_{blood}$ is the blood flow velocity in the blood vessel;
    $C_{tissue}$ is a speed of sound in soft tissue;
    $\alpha$ is an angle of incidence of the ultrasound waveform apparatus;
    $f_o$ is a resonant frequency of the ultrasound waveform apparatus; and
    $f_{doppler}$ is a frequency of Doppler shifted echo.

7. The method of claim 6, wherein the resonant frequency is between and includes 1.0 MHz and 10.0 MHz.

8. An apparatus comprising:
a memory; and
a processing device communicably coupled to the memory and to:
> transmit a signal directed to a blood vessel via a Doppler ultrasound waveform;
> receive a signal reflected from the blood vessel;
> determine whether the blood vessel is an artery or a vein based on a blood flow velocity in the blood vessel;
> determine a confidence level as to whether the blood vessel is an artery or a vein; and
> display, on a confidence gauge to indicate a confidence level of an artery or a vein, an indication of whether the blood vessel is an artery or a vein and an indication of the confidence level, wherein the apparatus is a self-contained, battery operated, wireless, and autoclavable Doppler ultrasound waveform apparatus comprising the confidence gauge on the apparatus, wherein the confidence gauge comprises a plurality of lights and wherein a number of illuminated lights of the plurality of lights indicates the confidence level.

9. The apparatus claim 8, wherein the Doppler ultrasound waveform having a resonant frequency between and including 1.0 MHz and 10.0 MHz.

10. A non-transitory computer readable storage medium including instructions that, when executed by a processing device, cause the processing device to perform operations comprising:
> transmitting a signal directed to a blood vessel via a self-contained, battery operated, wireless, and autoclavable Doppler ultrasound waveform apparatus comprising a confidence gauge to indicate a confidence level of an artery or a vein, wherein the confidence gauge comprises a plurality of lights and wherein a number of illuminated lights of the plurality of lights indicates the confidence level;
> receiving, by the Doppler ultrasound waveform apparatus, a reflected signal from the blood vessel;
> determining, by the processing device, whether the blood vessel is an artery or a vein based on a blood flow velocity in the blood vessel;
> determining, by the processing device, a confidence level as to whether the blood vessel is an artery or a vein,
> displaying the confidence level on the confidence gauge.

* * * * *